United States Patent [19]

Daly et al.

[11] Patent Number: 4,808,707

[45] Date of Patent: Feb. 28, 1989

[54] CHITOSAN ALGINATE CAPSULES

[75] Inventors: Mary M. Daly, West Chester, Pa.; Robert W. Keown, Wilmington; Dietrich W. Knorr, Newark, both of Del.

[73] Assignee: University of Delaware, Newark, Del.

[21] Appl. No.: 59,342

[22] Filed: Jun. 8, 1987

[51] Int. Cl.$^4$ .......... A61K 9/62; C12N 11/10; C08B 25/00
[52] U.S. Cl. .......... 536/3; 536/20; 514/963; 424/457; 424/461
[58] Field of Search .......... 536/20, 115, 3; 514/963; 424/461, 457

[56] References Cited

U.S. PATENT DOCUMENTS

| | | | |
|---|---|---|---|
| 4,352,883 | 10/1982 | Lim | 435/178 |
| 4,749,620 | 6/1988 | Rha et al. | 514/963 |

FOREIGN PATENT DOCUMENTS

| | | | |
|---|---|---|---|
| 0499026 | 1/1954 | Canada | 536/3 |
| 0152898 | 8/1985 | European Pat. Off. | |
| 1135856 | 12/1968 | United Kingdom | 536/3 |

OTHER PUBLICATIONS

King; "Tools for Building Stable Food Systems" Gum and Starch Technology 18th Annual Symposium, Cornell Univ., 11-17-83, pp. 19-25.
"Kelcoloid" Technical Bulletin DB-5, Kelco Laboratories, Clark, NJ 9-1984.
Knorr et al., Food Technology, 39 (10) 135-142, (1985).

Primary Examiner—Ronald W. Griffin
Assistant Examiner—Nancy S. Carson
Attorney, Agent, or Firm—Dean R. Rexford

[57] ABSTRACT

The permeability of the walls of chitosan alginate capsules is adjusted by substituting with esterified alginic acid a portion of the metal alginate normally used in the fabrication of such capsules.

3 Claims, No Drawings

CHITOSAN ALGINATE CAPSULES

The government has certain rights through sponsorship in part by the University of Delaware Sea Grant Program under grant number NA88 Project R/N-9 from the office of Sea Grant, National Oceanic and Atmospheric Administration (NOAA) U.S. Department of Commerce.

BACKGROUND OF THE INVENTION

1. Field of the Invention

The invention is in the field of capsules and encapsulation and relates to an improved process for encapsulating materials, especially biological materials such as living tissue, cells, or bacteria, wherein the materials remain viable and/or in a protected state within a membrane selectivity permeable to nutrients and to the metabolic products of the biological materials. Many other applications are seen, such as injectable capsules providing for the slow release of drugs, for example.

2. Description of the Related Art

The capsules of this invention are related to those art capsules resulting from interfacial reaction between polycations and polyanions.

Lim in U.S. Pat. No. 4,352,883 teaches a two-stage encapsulation of various biological materials wherein, in the main, droplets of an aqueous solution containing, for example, cationic sodium alginate and suspended active materials are introduced into a solution of a counter ion such as Ca++ in the form of the chloride, whereby to precipitate calcium alginate gel as a solid sphere incorporating the active material. Thereafter, the spheres are transferred to a solution of a polyanion such as polylysine, thus precipitating an organic anion-cation membrane around the sphere. Gel in the interior of the capsules is reliquified by immersing the spheres in a mixture of saline solution and citrate buffer of pH 7.4.

Rha and Rodriguez-Sanchez in European patent application No. 85101490 teach the direct formation of capsules having a liquid core by the process of mixing active material with one of two solutions, one solution containing an anionic polymer, the other a cationic polymer. The mixture containing the active material is then added dropwise to the other solution. The permeability of the membrane formed in this manner is controlled, according to patentees, by adjusting the concentration of the cationic and anionic polymers, the pH, the presence or absence of polyvalent counter ions, e.g. Ca++ or Ba++ or phospate as appropriate, the molecular weight of the polymers as well as through selection of the polymers themselves. Sodium alginate and chitosan, inter alia, are taught as anionic and cationic polymers, respectively.

Knorr et al in Food Technology, 39,(10): 135-142, 1985 reviewed the field, and references therein are incorporated by reference.

SUMMARY OF THE INVENTION

It has now been found that the permeability of the walls of chitosan alginate capsules can be adjusted by substituting a predetermined fraction of esterified alginic acid for a part of the metal alginate normally used in the fabrication of said capsules.

DESCRIPTION OF THE PREFERRED EMBODIMENTS

Although we do not wish to be bound by theory, we believe that the heart of the instant invention lies in the reduction of the density of ionic cross linking sites in the chitin alginate, cation-anion gel making up the walls of the capsule, whereby to provide a "looser" structure characterized by faster permeation rates. It is estimated that the permeation rate varies approximately as the ratio of esterified to unesterified alginic acid.

Esterified alginic acids are articles of commerce sold by the Kelco division of Merck & Company, Rahway, N.J. under the tradename "Kelcoloid." According to Kelco Technical Bulletin DB-5 and King, A. H.; "Tools for Building Stable Food Systems," Gum and Starch Technology 18th Annual symposium, D. L. Downing, Editor (Published by Merck & Co.), these products, available in various viscosities, are propylene glycol esters of alginic acid wherein 50 to 85% of all carboxyl groups are esterified. In this way some of the carboxyl groups of the alginic acid are blocked and the esters are often not precipitated at low pH or by calcium ions. It has been found that highly esterified products also do not react to an appreciable degree with chitosan as do less highly esterified or unmodified alginic acids. The products of the invention are derived from partially esterified alginic acids. Alginate esters of alcohols other than propylene glycol would behave similarly. Esters of the 1,2-isomer of propylene glycol are preferred.

The beneficial results of this invention are not limited to esterified alginates of particular viscosities; alginates of all viscosities appear to function.

EXAMPLE

Chitosan (Protan, Inc., Redmond, WA premium grade, 750 cps, 86% deacetylated) was autoclaved under water at 125 deg. C. and dissolved in aqueous citric acid. Other materials were added to produce a solution containing 30 g. chitosan, 260 millimoles citric acid, and 450 millimoles per liter $CaCl_2$ along with a trace of a mixture of the dyes brilliant blue an tartrazine (McCormick & Co., Baltimore, MD). The solution was stored under nitrogen.

Four viscosity grades of sodium alginate and 1,2-propylene glycol alginate, in the ratios by weight of 90:10 and 40:60 respectively, were dissolved in water at a concentration of 0.75 g. of mixture/100 ml, along with glucose as dispersing agent and plasticizer.

Capsules of about six mm diameter were formed on dropwise addition of the chitosan solutions through a Yale No. 14 stainless steel cannula into the alginate solutions. After 15 minutes of gentle agitation, the capsules were transferred with a nylon net to distilled water for a five minute wash and then into a hardening solution of 450 millimolar aqueous calcium chloride.

Thereafter capsules were tested, inter alia, for burst strength by uniaxial compression in a model TM Instron device (Instron Corp., Canton, MA). Capsules wherein 10% of the total carboxyl groups of the alginic acid were esterified, burst under an average force of 3278 grams.

It was observed that citric acid employed to solubilize the chitosan, permeated outwardly on average lowering the pH of the hardening solution from 6.1 to about 4.5 in 75 minutes whereas permeation from control capsules formed from unesterified alginic acid lowered the pH only to 4.7 under the same conditions. This corresponds approximately to a ratio of permeation rates of about 1.6. Similar effects were noted in the permeation of the encapsulated dyes. In art capsules only traces of dye permeated into the hardening solution whereas enough dye permeated from invention capsules to distinctly color the hardening solution.

Increased permeation was noted in capsules prepared from alginic acid esterified to the extent of as little as 5%: at 80% no capsules formed. With increasing proportions of esterified carboxyl groups, the strength decreases. Naturally the strength needed will depend on the use to which the capsules will be put. For most anticipated uses, alginic acid esterified to the extent of 10 to 60 percent will produce suitable capsules. It is preferred, for general use, to employ about 30% esterified alginic acid.

Although the invention has been illustrated with propylene glycol esters, it is believed that other esters would be operable. It is expected, for example, that esterification with long chain alcohols would increase hydrophobicity, whereas those containing multiple hydroxyl groups such as mono-esterified glycerol would be expected to increase hydrophilicity. In all cases the permeability will be increased over that of capsules derived from unesterified alginic acid.

Having now described our invention, we claim:

1. A capsule of chitosan alginate wherein said alginate is 10 to 60% esterified with 1,2-propylene glycol to increase the permeability of the walls of said capsule.

2. The capsule of claim 1 wherein the alginate is 30% esterified.

3. The capsule of claim 1 hardened with calcium chloride.

* * * * *